United States Patent
Krüger et al.

(10) Patent No.: US 7,603,169 B2
(45) Date of Patent: Oct. 13, 2009

(54) STIMULATION ELECTRODE WITH POROUS COATING

(75) Inventors: Frank Krüger, Bruchköbel (DE); Heiko Specht, Aschaffenburg (DE); Hans-Jürgen Wachter, Rödermark (DE); Oliver Keitel, Aschaffenburg (DE)

(73) Assignee: W.C. Heraeus GmbH, Hanau (DE)

( * ) Notice: Subject to any disclaimer, the term of this patent is extended or adjusted under 35 U.S.C. 154(b) by 580 days.

(21) Appl. No.: 11/378,902

(22) Filed: Mar. 17, 2006

(65) Prior Publication Data

US 2006/0270924 A1    Nov. 30, 2006

(30) Foreign Application Priority Data

Mar. 18, 2005    (DE)    ......... 10 2005 013 066

(51) Int. Cl.
 *A61B 5/02*    (2006.01)
(52) U.S. Cl. .................. 600/510; 600/372; 607/115
(58) Field of Classification Search ............ 600/372
 See application file for complete search history.

(56) References Cited

U.S. PATENT DOCUMENTS

| 4,502,492 A | 3/1985 | Bornzin |
| 5,318,572 A | 6/1994 | Helland et al. |
| 5,836,874 A * | 11/1998 | Swanson et al. ......... 600/374 |
| 6,023,638 A * | 2/2000 | Swanson .................. 600/510 |
| 2004/0220652 A1 | 11/2004 | Zhou et al. |
| 2005/0059862 A1 * | 3/2005 | Phan ....................... 600/176 |

FOREIGN PATENT DOCUMENTS

| DE | 42 07 368 A1 | 2/1993 |
| EP | 0 115 778 A1 | 1/1984 |
| EP | 0 116 280 A1 | 1/1984 |
| EP | 0 117 972 A1 | 1/1984 |
| EP | 0 054 781 B1 | 10/1984 |

OTHER PUBLICATIONS

J. Riedmuller et al. "Improvement of Stimulation and Sensing Performance of Bipolar Pacemaker Leads", *Proceedings of the 14th annual conference of the IEEE/EMBSI*, pp. 2364-2365, (1992).

* cited by examiner

*Primary Examiner*—Carl H. Layno
*Assistant Examiner*—Jon-Eric C. Morales
(74) *Attorney, Agent, or Firm*—Panitch Schwarze Belisario & Nadel LLP

(57) ABSTRACT

An electrode for medical applications is provided with a PtIr coating which is at least partly porous. The coating contains more than 20% iridium by weight and at least 100 ppm Pt. The coated areas of the electrode exhibit an electrochemical capacitance of more than 5 mF/cm$^2$ in physiological saline solution at 37° C. and a measurement frequency of 100 mHz. A sputter process is suitable for this purpose, in which a porous platinum-iridium layer is deposited on the electrode by simultaneously sputtering at least one iridium target and at least one platinum target.

13 Claims, 12 Drawing Sheets

STIMULATION ELECTRODE WITH POROUS COATING

BACKGROUND OF THE INVENTION

The present invention relates to an electrode for medical applications, particularly for the stimulation of tissue. The invention also relates to a suitable manufacturing process for the electode. Such electrodes are, as a rule, coated.

European published patent applications EP 117 972 A, EP 116 280 A, and EP 115 778 A disclose electrodes for medical applications which have porous coatings of titanium nitride.

According to European Patent EP 0 054 781, a heart pacemaker electrode with low stimulation power is prepared which has a coating of platinum, indium, or a platinum-iridium alloy containing up to 20% by weight of iridium. The coating is performed galvanically in the examples.

According to J. Riedmüller et al., *Proceedings of the 14th annual conference of the IEEE/EMBS*, pp. 2364-2365, Orlando (1992), the surface of the coating is increased in order to achieve a higher capacitance and thus to decrease the impedance of the transition from the electrode to the cell. The surface area can thereby be increased, either by applying platinum-iridium spheroids and sintering them, or by coating a smooth surface with platinum black. As another alternative, iridium can be applied using a sputter technique.

From German Patent DE 42 07 368, a heart pacemaker electrode is known with a fractally sputtered iridium and Ir/Pt alloy coating. Iridium oxidizes during normal use to $IrO_2$. Particularly for neurological applications, in which an excitation of significantly higher frequency than that of cardiological stimulation is used, this represents a significant problem, since the conversion of Ir to $IrO_2$ can result in a degradation and dissolution of a layer in the body.

Furthermore, a platinum-black-coated electrode is known from U.S. Pat. No. 4,502,492. Platinum, as a noble metal, is on the one hand significantly more expensive than iridium. Moreover, however, the catalytic effect of platinum is more extensive, so that side effects may occur during contact with tissues.

BRIEF SUMMARY OF THE INVENTION

It is an object of the present invention to provide a coating for stimulation electrodes, using a minimal amount of noble metal, for increasing their electrochemical capacitance while simultaneously minimizing their catalytic activity, whereby the impedance during the stimulation should remain stable even under anodic load.

The object is achieved with a sputter process, in which the coating occurs by simultaneous deposition from at least two sputter targets, including at least one Ir and at least one Pt target, thus allowing the adjustment of a defined alloy. The stoichiometry of the PtIr can thus be varied in the coating as the layer thickness increases. Thu, a sputter process is provided in which a uniform alloy, or one with a gradient, can be generated on an object to be sputtered with the simultaneous use of Ir and Pt targets in one sputter process.

This process particularly allows the manufacture of a one-phase platinum-iridium alloy in which the iridium is completely dissolved in the platinum.

In this way, a stimulation electrode can be manufactured which achieves the above object with a coating of platinum-iridium alloy. The alloy composition can be freely selected and is not predetermined by the composition of the sputter target.

The platinum portion can be low in order to minimize catalytic activity as well as cost, wherein iridium is the significant component. Such electrodes with low platinum content exhibit a high electrochemical capacitance, for example more than 5 $mF/cm^2$ in a physiological saline solution at 37° C. and a measurement frequency of 100 mHz.

The simultaneous sputter process according to the invention with two targets also allows a rational alloy deposition with individually adjustable alloy composition on the individual object. Thus, a sequential manufacture is possible with differently defined alloys as coatings.

Alloys with 5 to 60% platinum have proven particularly advantageous. Particularly preferred is a Pt content of 10 to 40%.

One embodiment of the present invention is an electrode for medical applications which is partly coated with a porous platinum-iridium layer, wherein the coating contains at least 20% by weight of iridium, preferably more than 40% by weight of iridium, particularly more than 60% by weight of iridium, and most preferred more than 80% by weight of iridium, and contains at least 100 ppm of platinum, and wherein the coated area exhibits an electrochemical capacitance of more than 5 $mF/cm^2$ in physiological saline solution at 37° C. and a measurement frequency of 100 mHz.

In additional preferred embodiments usable together or in combination:
1. the platinum is fully dissolved in the iridium of the platinum-iridium coating; and/or
2. a porous platinum-iridium coating exhibits a gradient of stoichiometry, particularly a gradient in which at least one alloy component varies by at least 10% by weight across the thickness of the layer.

Such electrodes are suitable for use as heart pacemaker electrodes, neurostimulation electrodes, or muscle stimulation electrodes. According to the invention, these electrodes can be manufactured sequentially, customized to the individual case.

According to Riedmüller et al, an increase in the electrochemical capacitance is achieved by coating the electrode body with PtIr spheres. However, due to the mechanical properties of PtIr alloys, the manufacture of PtIr spheres is only possible up to an Ir content of 30% by mass. In order to further minimize the use of expensive platinum, the Ir portion should be greater than 30%, which is enabled by the coating of desired compositions using the simultaneous deposition of at least two targets.

According to the invention, the noble metal is particularly efficiently used, because on the one hand the mass of noble metal can be kept particularly small, whereby, however, the electrochemical capacitance is maximized and therefore the phase boundary impedance between the electrode and the tissue is minimized (Table 1).

TABLE 1

Electrochemical capacitance at f = 1 Hz for different noble metal weights used

| | Coating mass | Capacitance at f = 1 Hz |
|---|---|---|
| Uncoated PtIr | — | 0.07 $mF/cm^2$ |
| PtIr coating per J. Riedmüller et al | about 10 mg | 2 $mF/cm^2$ |
| PtIr coating of the invention | less than 0.5 mg | 19 $mF/cm^2$ |

With the simultaneous deposition from at least two targets according to the invention, it is furthermore possible to dope Ir coatings specifically with Pt, wherein the Pt doping is at least 100 ppm. The oxidation of the iridium to $IrO_2$ can thereby be prevented during use as a stimulation electrode. There is no risk of degradation and possible dissolution of the porous PtIr coating.

Stimulation electrodes of the present invention are particularly suitable for use as neurostimulation electrodes, since here an increased frequency is used for stimulation in comparison with cardiac stimulation, and the risk of conversion of the Ir to $IrO_2$ is particularly high.

Additional suitable applications are use of the electrodes as heart pacemaker electrodes or as peripheral muscle stimulation electrodes.

The preferred base material of the electrodes is at least one selected from titanium, tantalum, platinum, platinum-iridium, and a cobalt-chromium alloy. The preferred iridium content of the platinum-iridium coating is more than 60% by weight, preferably greater than 80% by weight.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

The cyclovoltammograms (CVs) shown in FIGS. 1-9 for iridium-coated heart pacemaker (HPM) electrodes were created analogously to the procedure described in *Electroanalytical Chemistry and Interfacial Electrochemistry*, 55:375-381, Elsevier Sequoia S. A., Lausanne (1974) in 1 M $H_2SO_4$ at a scan speed of 40 mV/s. The potential range for therefor was between −0.3 and +1.2 V measured against a standard calomel electrode (SCE).

An increase in the anodic and the cathodic current can be detected in the potential range between about 0.6 and 1.2 V, from the first to the 100th cycle with the iridium-coated electrode. This process is reversible. This is considered to be an "activation" of the Ir coating.

Figure 1:
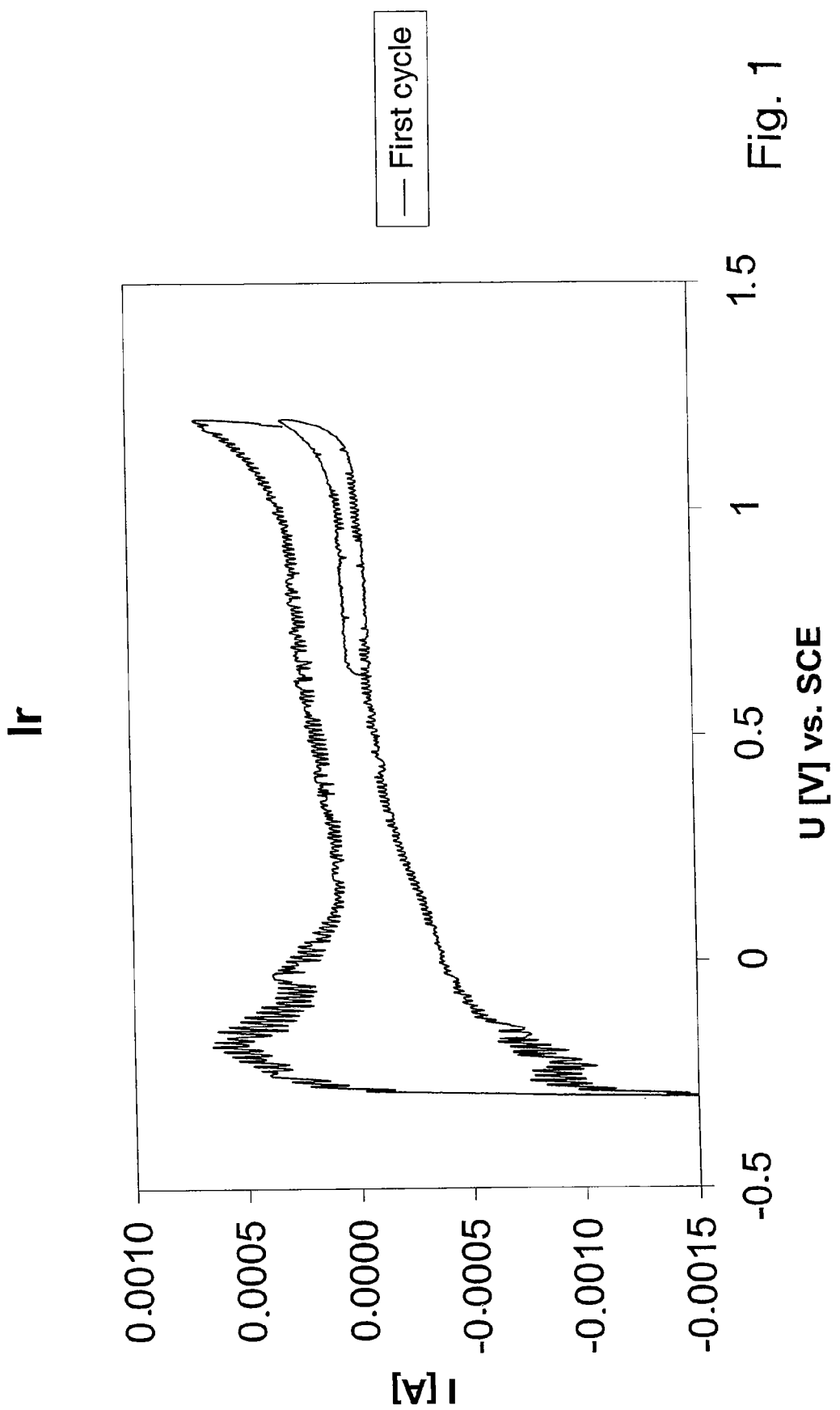
FIG. 1 is a cyclovoltammogram (CV) of the first cycle of an iridium electrode measured against a standard calomel electrode (SCE)
Figure 2:
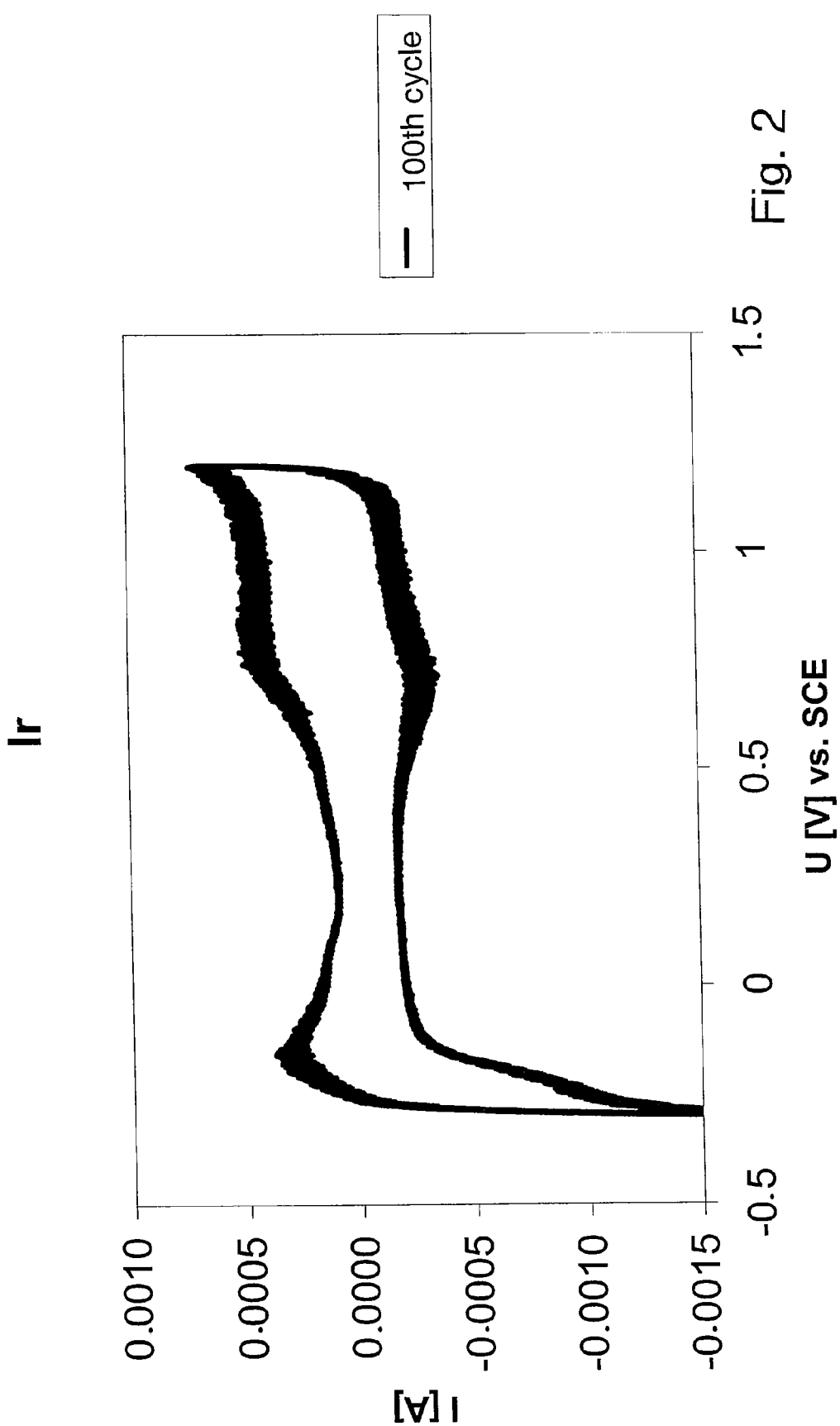
FIG. 2 is a CV of the 100th cycle of an iridium electrode measured against a standard calomel electrode (SCE)
Figure 3:
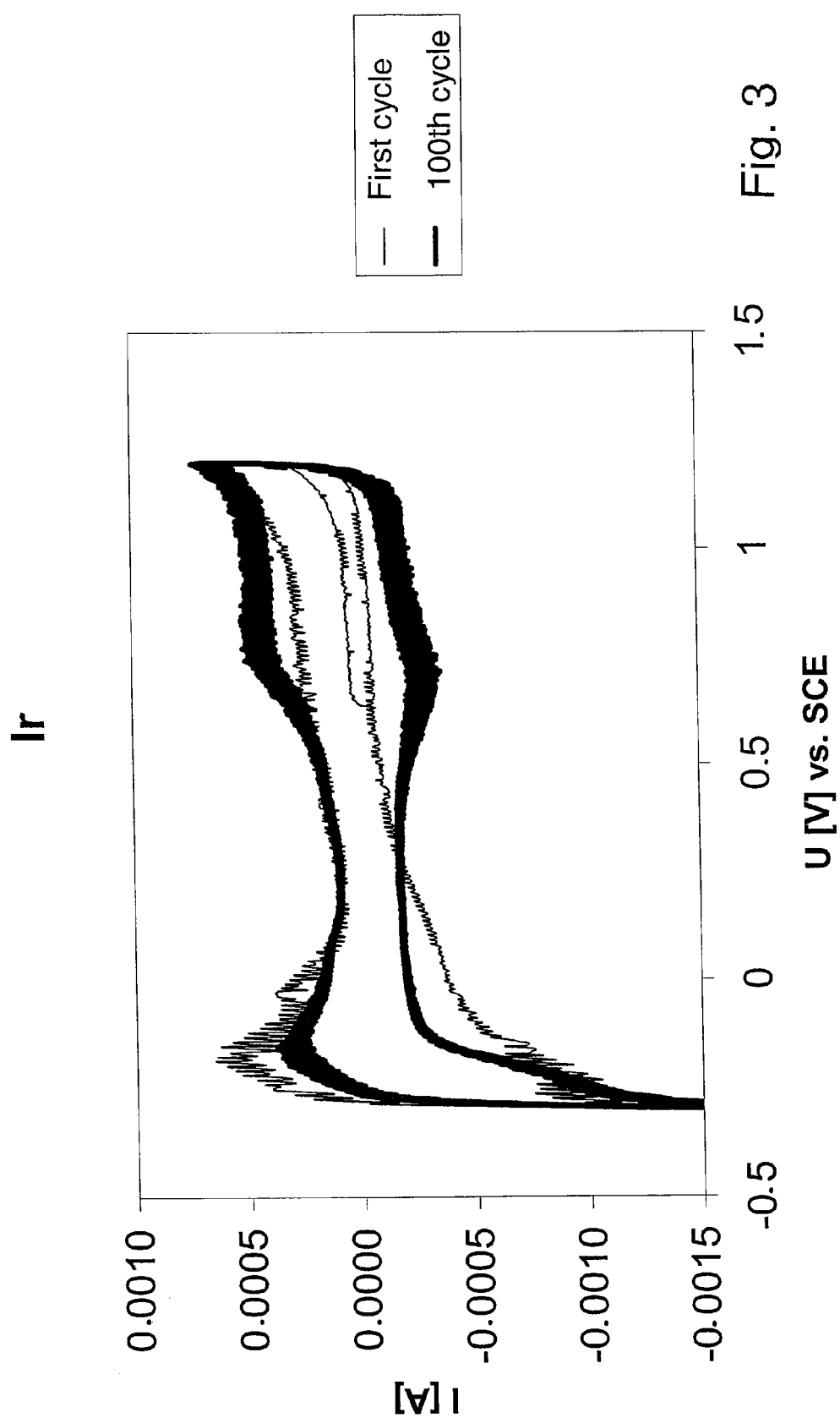
FIG. 3 is a superimposition of FIGS. 1 and 2.
Figure 4:
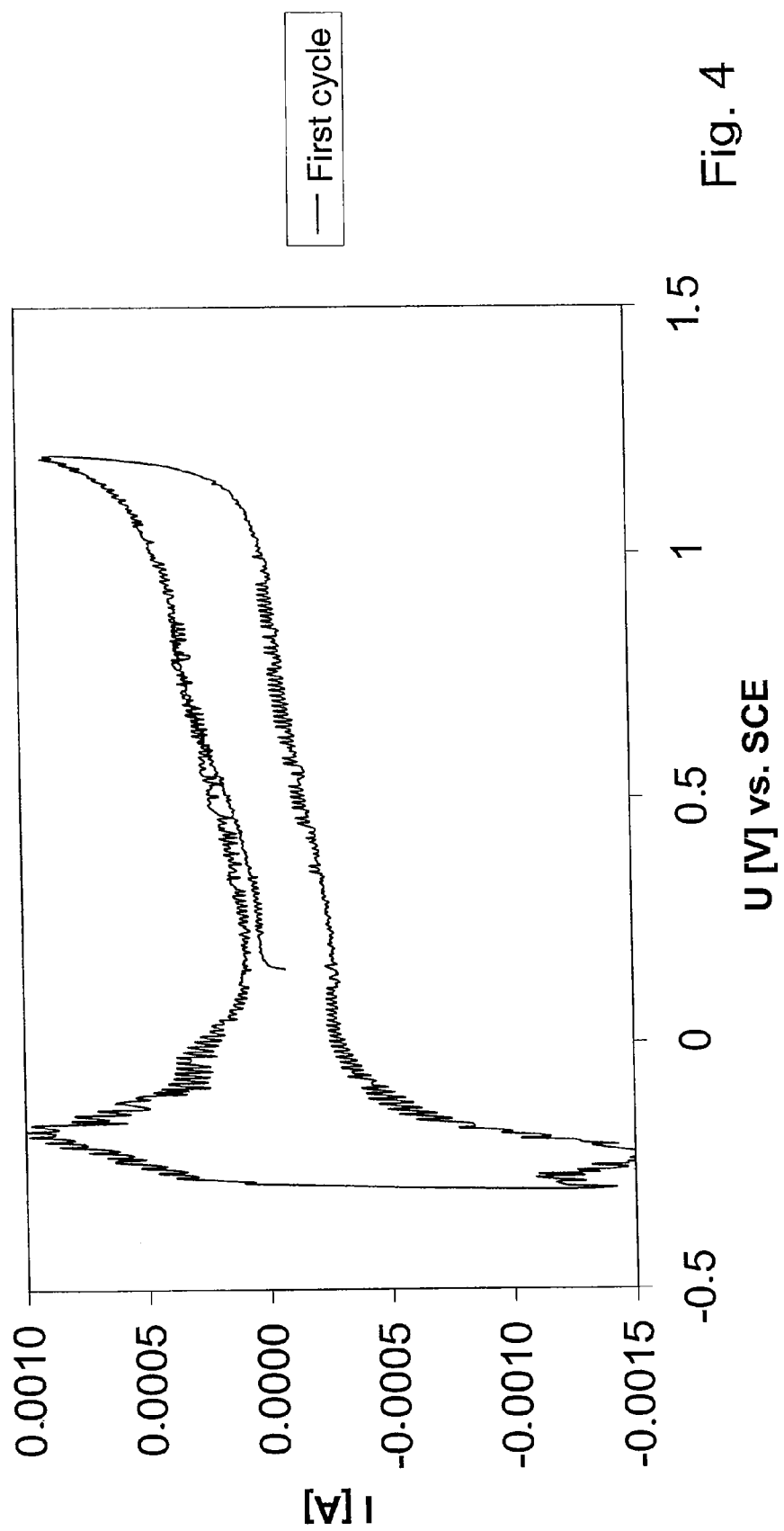
FIG. 4 is a CV of the first cycle of an iridium electrode doped with 5% platinum measured against a standard calomel electrode (SCE)
Figure 5:
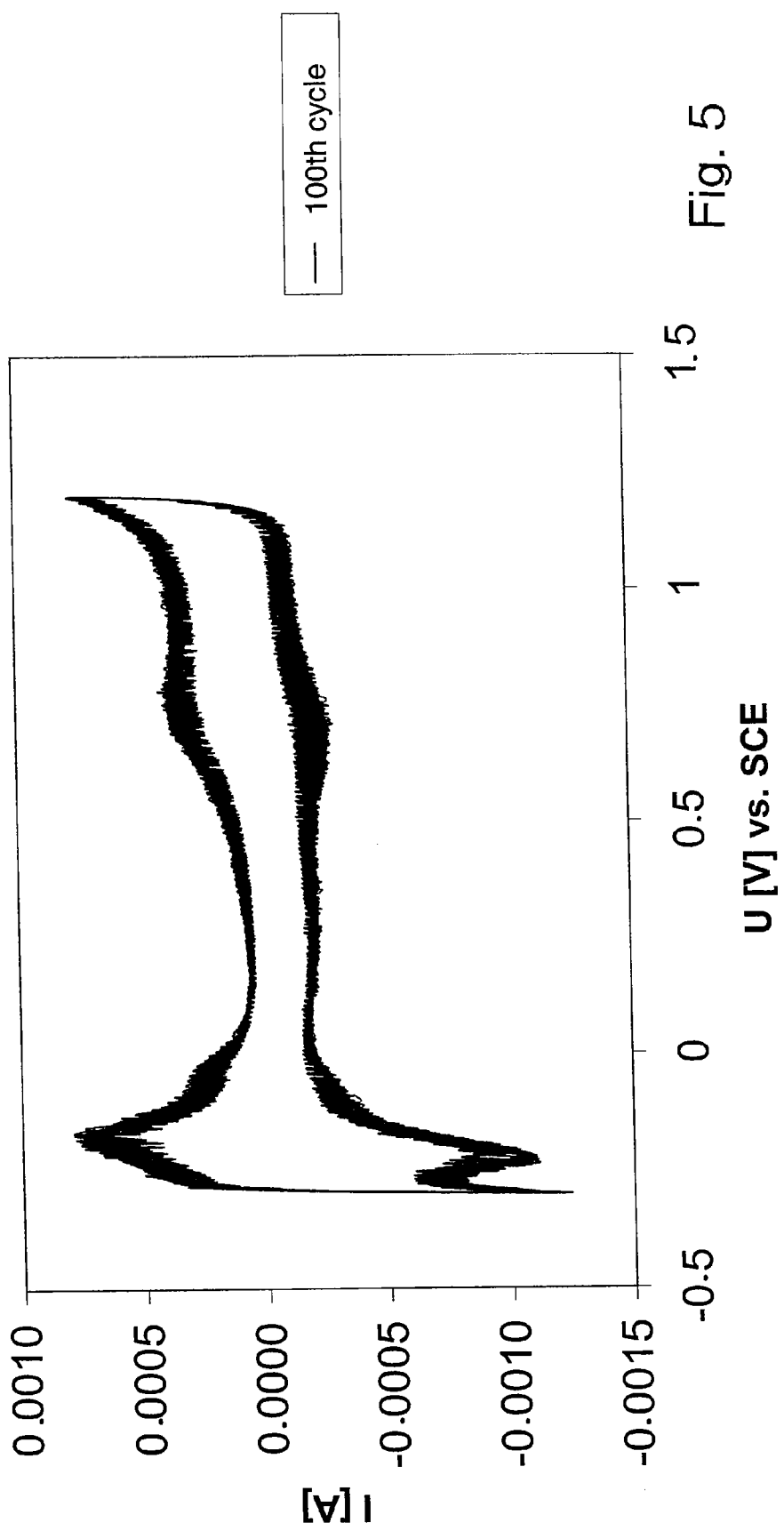
FIG. 5 is a CV of the 100th cycle of an iridium electrode doped with 5% platinum measured against a standard calomel electrode (SCE)
Figure 6:
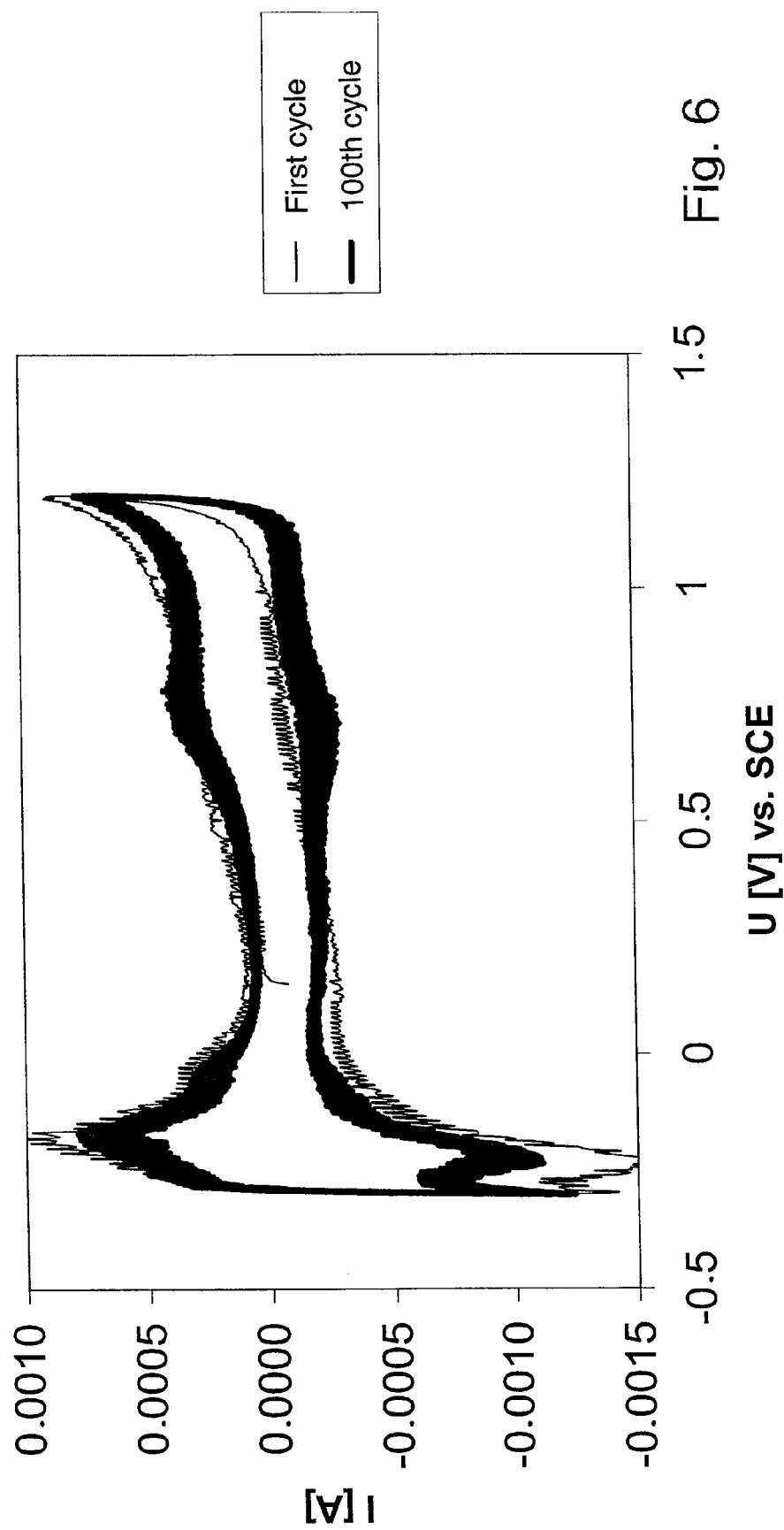
FIG. 6 is the superimposition of FIGS. 4 and 5.
Figure 7:
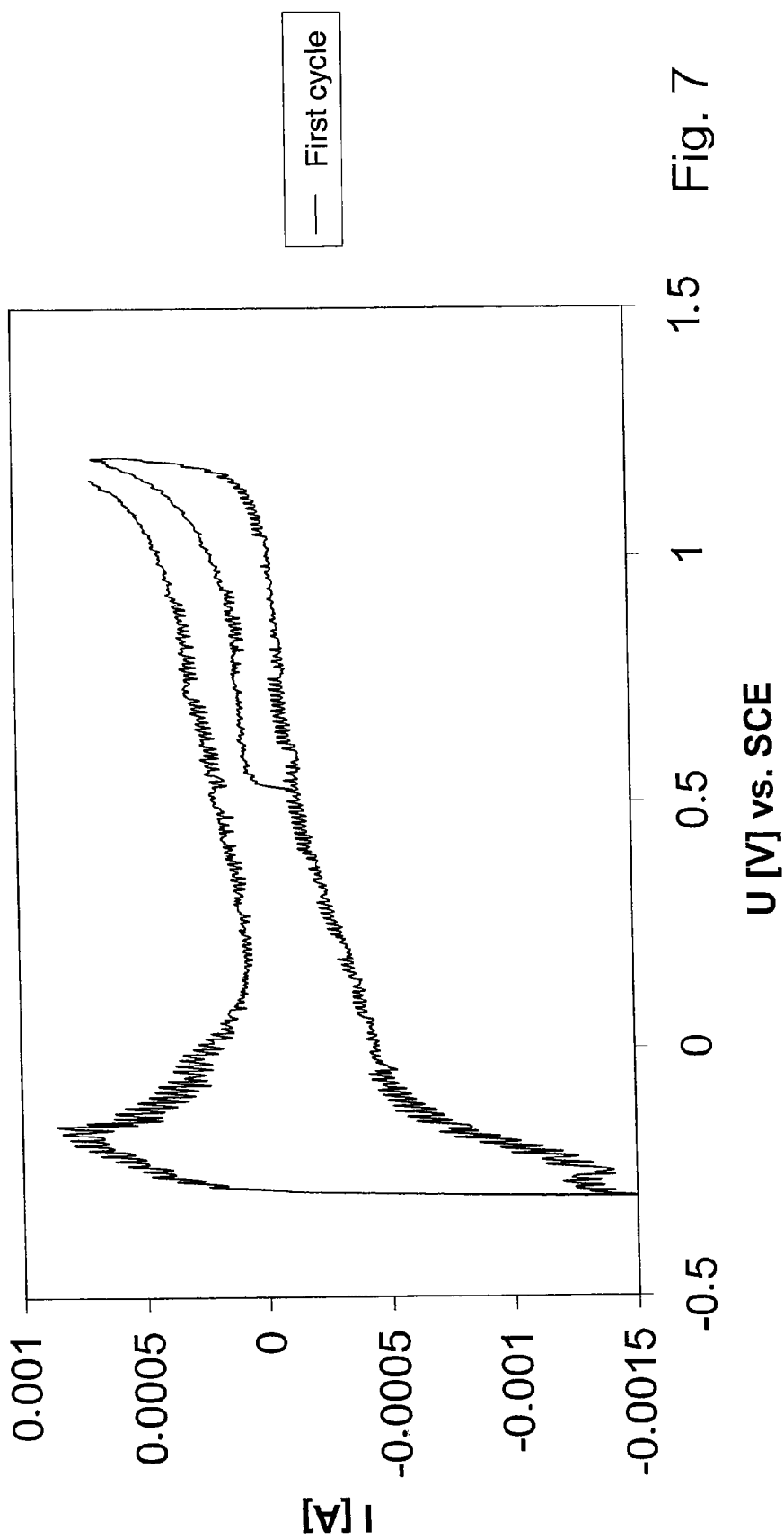
FIG. 7 is a CV of the first cycle of an iridium electrode doped with 10% platinum measured against a standard calomel electrode (SCE)
Figure 8:
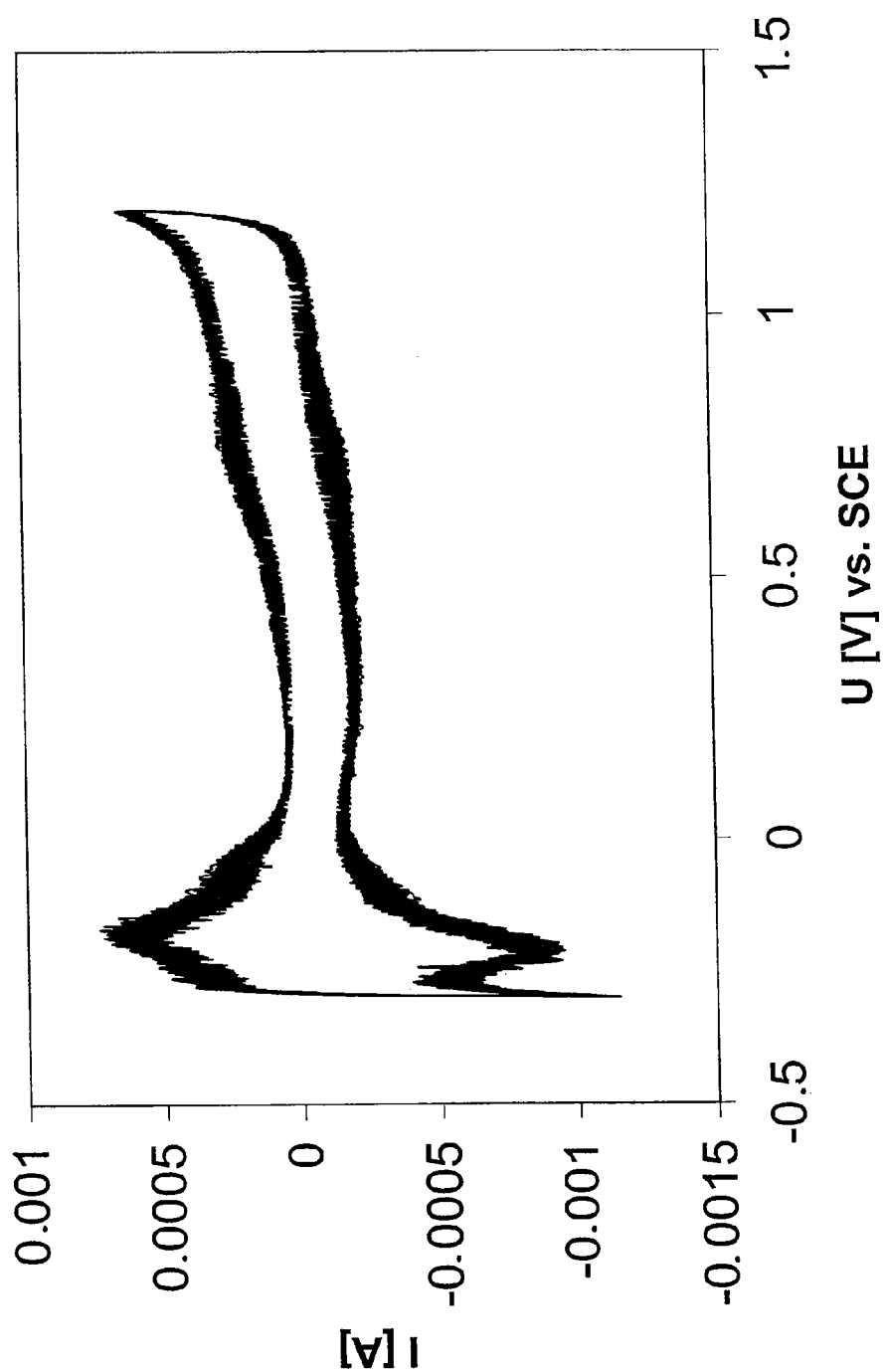
FIG. 8 is a CV of the 100th cycle of an iridium electrode doped with 10% platinum measured against a standard calomel electrode (SCE)
Figure 9:
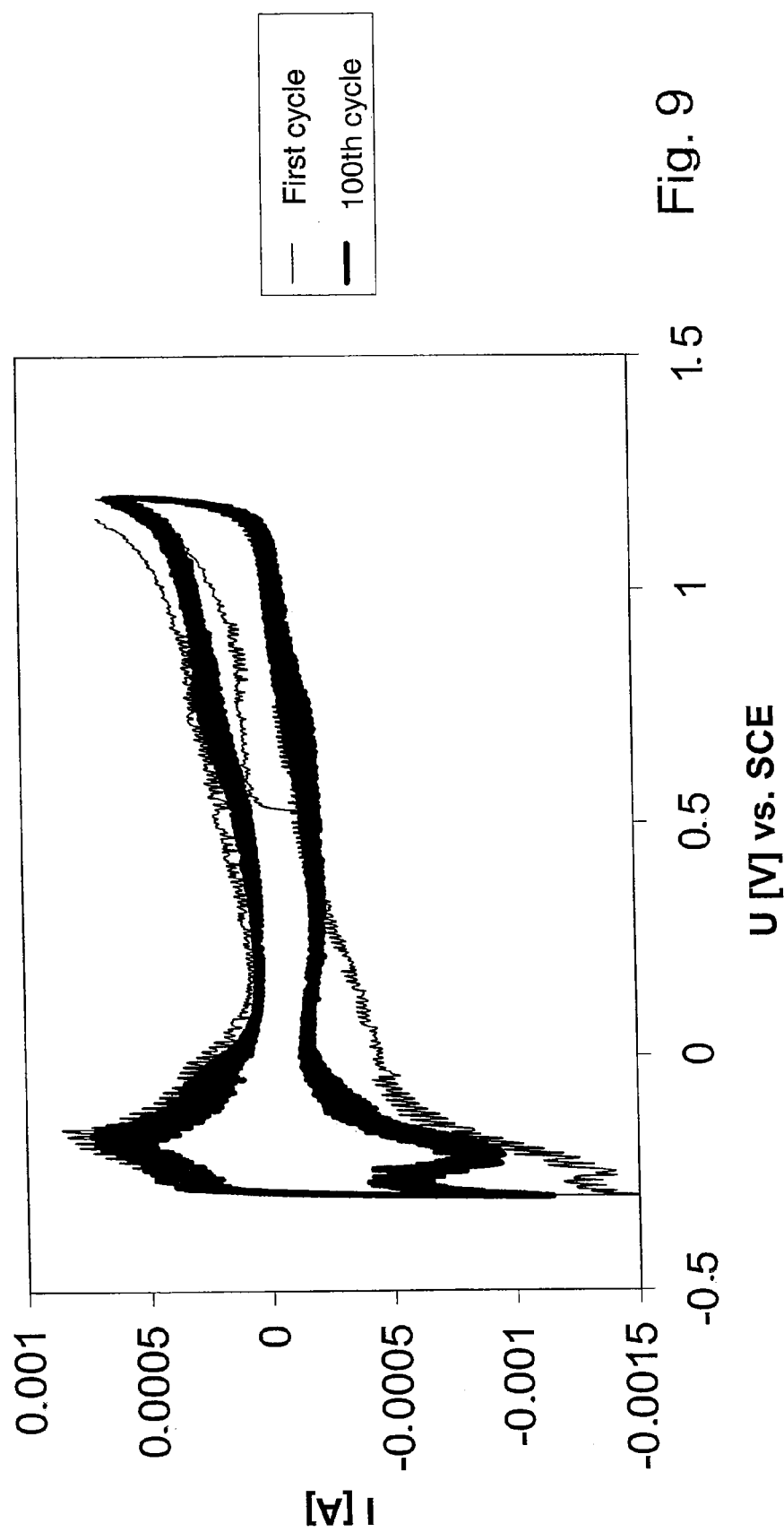
FIG. 9 is the superimposition of FIGS. 7 and 8.

FIGS. 4 through 9 illustrate the influence of a platinum doping on the electrochemical behavior of the electrodes. Even a platinum concentration of approximately 5% significantly protects the electrode from activation. The current/voltage curve remains nearly constant over 100 cycles. Thus, in contrast with electrodes having a pure iridium coating, there is no increase in current in the anodic potential range over 100 cycles. With a 10% platinum doping there is even a slight decrease in the anodic current by the 100th cycle. (FIGS. 7 through 9).

MANUFACTURING EXAMPLE

Figure 10:
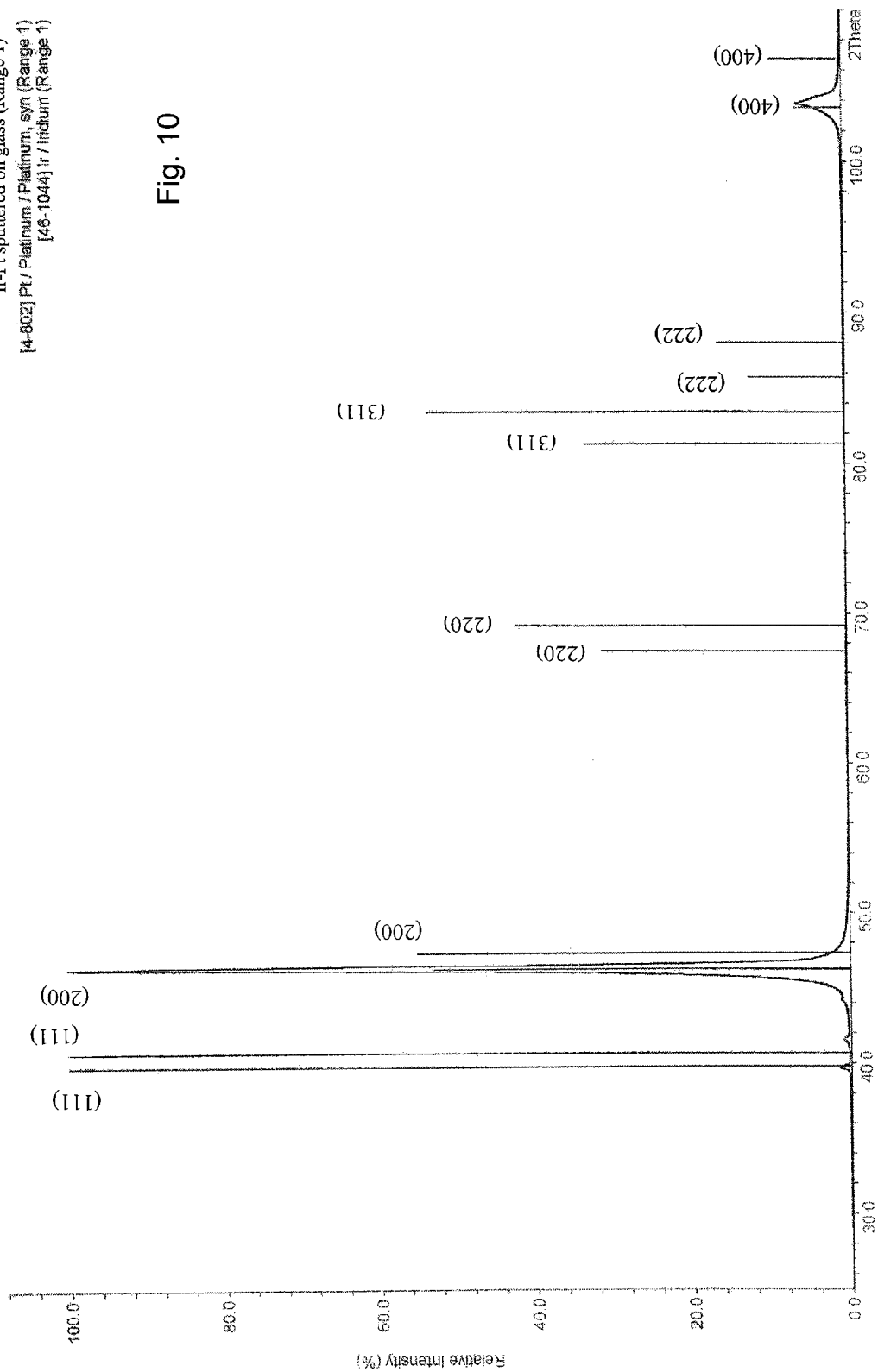
FIG. 10 is a powder diffractogram of an iridium-platinum alloy sputtered on glass, where the coating consists of a one-phase alloy.

A sputtering apparatus is equipped with two devices for two targets. One platinum and one iridium target are arranged in the sputtering apparatus. A glass body is coated in this apparatus. The coating is analyzed with a powder diffractometer system (FIG. 10). The peak of the alloy at (200) is minimally offset towards the iridium peak in comparison with a platinum peak. The alloy peak exhibits no separation, not even a shoulder. This leads to the conclusion that the iridium is fully dissolved in the platinum, such that the platinum structure remains largely unchanged.

Figure 11:
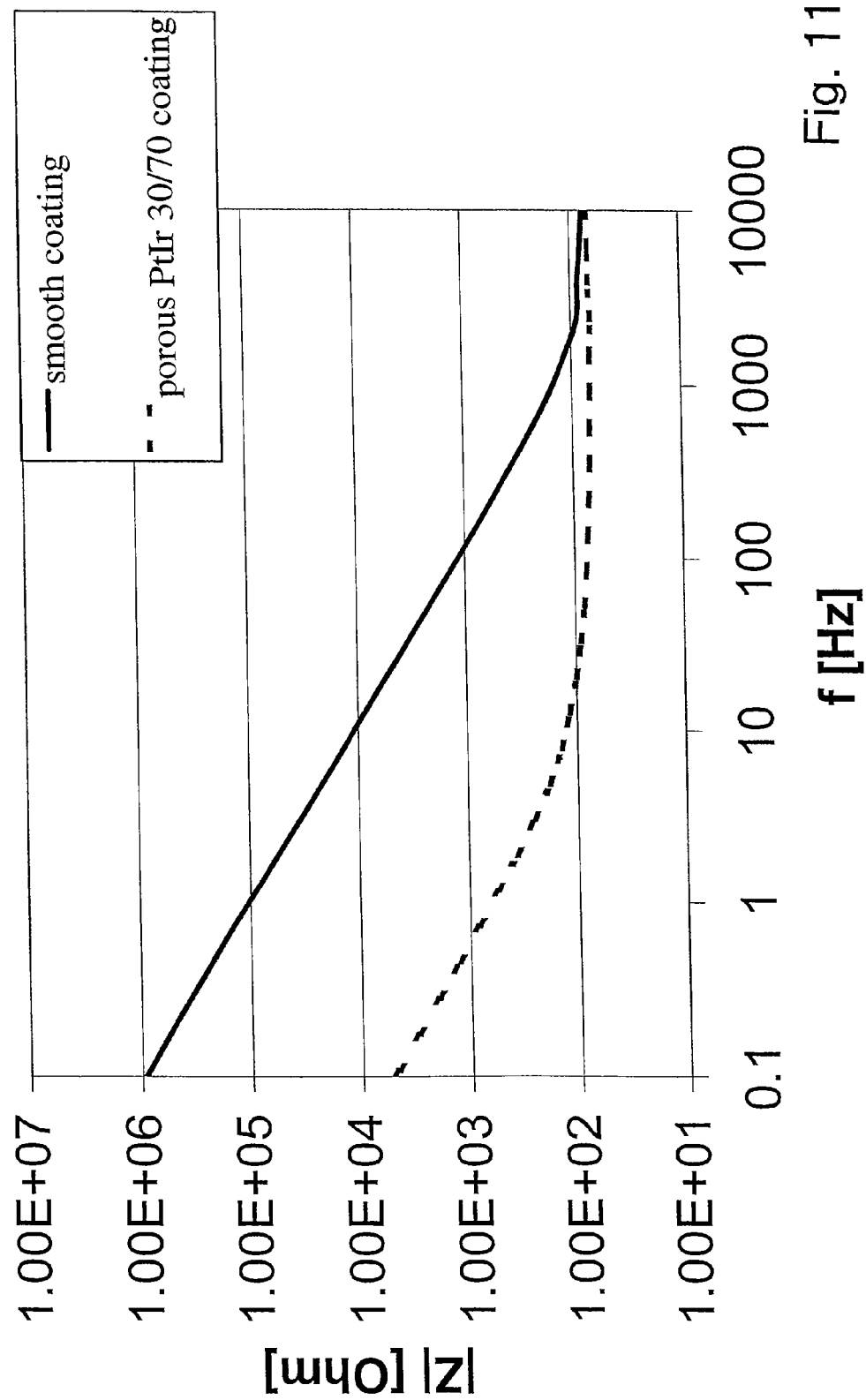
FIG. 11 is a graph comparing the impedance as a function of the frequency for stimulation electrodes having smooth and porous coatings of PtIr 30/70.

According to the invention, a porous alloy deposition occurs which, as seen in FIG. 11, exhibits a drastically reduced impedance in a broad range of frequencies. In particular, an increase in impedance only becomes noticeable in the frequency range between 0.1 and 10 Hz, while an increase for smooth coating from galvanic deposition already occurs at over 1000 Hz. In contrast, the impedance of the porous platinum-iridium alloy remains nearly constant as low as 100 Hz and changes only slightly down to approximately 10 Hz. With the porous alloy layer obtained by simultaneous sputtering according to the present invention, a drastic improvement in stimulation properties is assured, such as pulse transmission at the electrode/tissue interface, at a frequency in the range between 0.1 and 1000 Hz. With a smooth coating obtained by galvanic deposition, 1.8 µF was measured at 100 Hz, 2 µF at 1 Hz, and 5 µF at 10 mHz, whereas with the porous coating according to the present invention, 120 µF was measured at 100 Hz, 279 µF at 1 Hz, and 409 µF at 10 mHz. The porous layer used here according to the invention is a 70:30 iridium-platinum alloy. In the alloy range from 70:30 to 30:70 no differences can be found.

APPLICATION EXAMPLE

Figure 12:
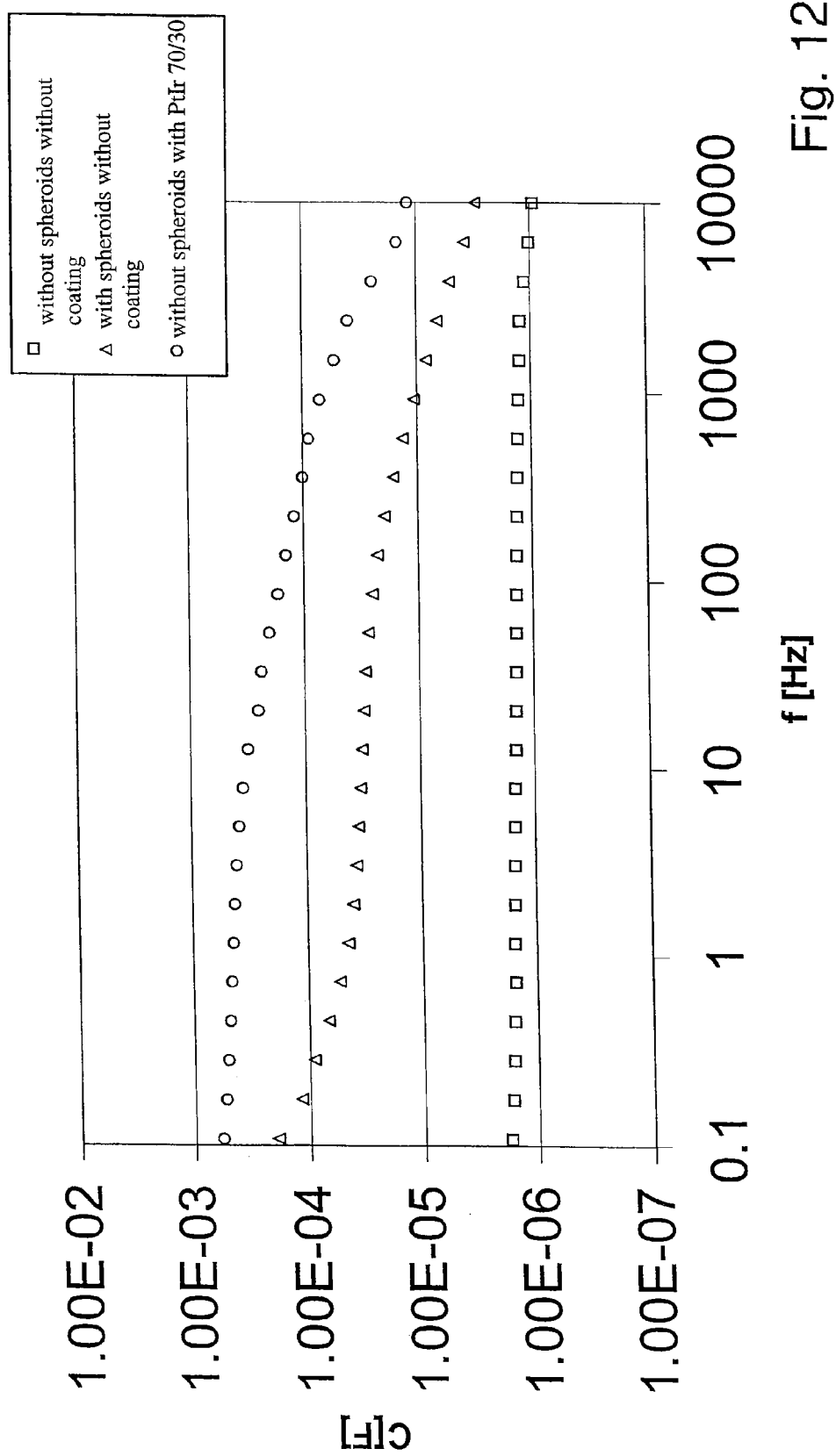
FIG. 12 is a graph of capacitance vs. frequency showing the capacitance increase due to coating with spheroids and the additional capacitance increase with an iridium-platinum alloy in the range of 70:30 to 30:70, applied to a heart pacemaker electrode according to the present invention.

In FIG. 12 the capacitance increase in comparison with an uncoated HPM electrode is shown. Even with a spheroid deposition, an increase in capacitance can be achieved. Furthermore, an additional increase in capacitance can be achieved by coating with a platinum-iridium alloy which is deposited in a PVD process using two sputter targets, one of iridium and the other of platinum. The uncoated electrode had a capacitance of 1.4 µF at 100 Hz and 1.6 µF at 1 Hz. With a deposit of 10 mg of platinum-iridium spheroids (balls) the capacitance at 100 Hz increased to 22.9 µF and at 1 Hz to 44.6 µF. In contrast, with a lower use of noble metal, an additional increase in capacitance was achieved by depositing on the substrate a 0.5 mg coating from an iridium target and a platinum target with simultaneous PVD coating. At 100 Hz a capacitance of 143 µF was thereby achieved, and at 1 Hz a capacitance of 440 µF was achieved. The ratio of capacitance at 100 Hz per noble metal used is therefore more than 60 times larger with the present invention than for a coating with spheroids, and at 1 Hz the ratio is even almost 200 times greater. Consequently, the deposition according to the present process is significantly more efficient than coating with spheroids.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An electrode for medical applications, comprising a base body at least partially coated with a porous platinum-iridium (PtIr) alloy coating, wherein the coating contains more than 20% iridium by weight and at least 100 ppm platinum (Pt) and the coated area of the base body exhibits an electrochemical capacitance of more than 5 mF/cm$^2$ in a physiological saline solution at 37° C. and a measurement frequency of 100 mHz.

2. The electrode according to claim 1, wherein the base body comprises at least one metal selected from titanium (Ti), tantalum (Ta), Pt (platinum), PtIr, and a cobalt-chromium (CoCr) alloy.

3. The electrode according to claim 1, wherein the coating contains less than 1 mg noble metal.

4. The electrode according to claim 3, wherein the PtIr alloy coating contains more than 40% iridium by weight.

5. The electrode according to claim 4, wherein the PtIr alloy coating contains more than 60% iridium by weight.

6. The electrode according to claim 5, wherein the PtIr alloy coating contains more than 80% iridium by weight.

7. The electrode according to claim 1, wherein in the PtIr alloy coating, the platinum is fully dissolved in the iridium.

8. The electrode according to claim 1, wherein the porous PtIr alloy coating has a gradient in stoichiometry.

9. The electrode according to claim 8, wherein a content of at least one alloy component in the porous PtIr alloy coating varies by at least 10% across the thickness of the coating.

10. The electrode according to claim 1, comprising a heart pacemaker electrode.

11. The electrode according to claim 1, comprising a neurostimulation electrode.

12. The electrode according to claim 1, comprising a peripheral muscle stimulation electrode.

13. A sputter process for manufacture of an electrode for medical applications, the process comprising depositing a porous platinum-iridium coating on a base body of the electrode by simultaneously sputtering at least one iridium target and at least one platinum target, wherein stoichiometry of the platinum-iridium coating is varied during the coating process.

* * * * *

UNITED STATES PATENT AND TRADEMARK OFFICE
CERTIFICATE OF CORRECTION

PATENT NO. : 7,603,169 B2 Page 1 of 1
APPLICATION NO. : 11/378902
DATED : October 13, 2009
INVENTOR(S) : Krüger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 790 days.

Signed and Sealed this

Fifth Day of October, 2010

David J. Kappos
*Director of the United States Patent and Trademark Office*